United States Patent
Park

(10) Patent No.: US 11,096,917 B2
(45) Date of Patent: Aug. 24, 2021

(54) COMPOSITION FOR PREVENTING OR TREATING MUSCLE DISEASES, COMPRISING SUBERIC ACID OR PHARMACEUTICALLY ACCEPTABLE SALT THEREOF AS ACTIVE INGREDIENT

(71) Applicant: INDUSTRY-ACADEMIC COOPERATION FOUNDATION, YONSEI UNIVERSITY, Seoul (KR)

(72) Inventor: Tae Sun Park, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 114 days.

(21) Appl. No.: 16/476,396

(22) PCT Filed: Jan. 5, 2018

(86) PCT No.: PCT/KR2018/000300
§ 371 (c)(1),
(2) Date: Jul. 8, 2019

(87) PCT Pub. No.: WO2018/128479
PCT Pub. Date: Jul. 12, 2018

(65) Prior Publication Data
US 2021/0023035 A1 Jan. 28, 2021

(30) Foreign Application Priority Data
Jan. 6, 2017 (KR) .................. 10-2017-0002501

(51) Int. Cl.
| | |
|---|---|
| A61K 31/20 | (2006.01) |
| A61K 9/00 | (2006.01) |
| A61K 47/44 | (2017.01) |
| A61K 47/26 | (2006.01) |
| A61K 47/32 | (2006.01) |
| A61K 47/18 | (2017.01) |
| A61K 47/10 | (2017.01) |
| A61K 31/07 | (2006.01) |
| A61K 31/355 | (2006.01) |
| A61K 33/30 | (2006.01) |
| A61K 33/26 | (2006.01) |
| A61K 33/06 | (2006.01) |
| A61K 33/00 | (2006.01) |
| A61K 31/714 | (2006.01) |
| A61K 31/4415 | (2006.01) |
| A61K 31/51 | (2006.01) |
| A61K 31/375 | (2006.01) |
| A61K 31/455 | (2006.01) |
| A61K 31/4188 | (2006.01) |
| A23K 20/105 | (2016.01) |

(52) U.S. Cl.
CPC ............ *A61K 31/20* (2013.01); *A23K 20/105* (2016.05); *A61K 9/0014* (2013.01); *A61K 9/0056* (2013.01); *A61K 31/07* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/714* (2013.01); *A61K 33/00* (2013.01); *A61K 33/06* (2013.01); *A61K 33/26* (2013.01); *A61K 33/30* (2013.01); *A61K 47/10* (2013.01); *A61K 47/18* (2013.01); *A61K 47/26* (2013.01); *A61K 47/32* (2013.01); *A61K 47/44* (2013.01)

(58) Field of Classification Search
None
See application file for complete search history.

(56) References Cited

U.S. PATENT DOCUMENTS

| 6,100,287 A | 8/2000 | Stevens et al. |
|---|---|---|
| 2006/0189566 A1 | 8/2006 | Komatsu et al. |

FOREIGN PATENT DOCUMENTS

| KR | 2015-0024586 | 3/2015 |
|---|---|---|
| KR | 2015-0071932 | 6/2015 |
| KR | 2015-0142536 | 12/2015 |
| WO | WO 92/12960 | 8/1992 |
| WO | WO 03/071884 | 9/2003 |

OTHER PUBLICATIONS

International Search Report and Written Opinion issued in International Patent Application No. PCT/KR2018/000300, dated May 8, 2018. (English Translation).

*Primary Examiner* — Kristin A Vajda
(74) *Attorney, Agent, or Firm* — Norton Rose Fulbright US LLP

(57) ABSTRACT

The present invention relates to a composition for preventing or treating a muscular disease or improving muscle function. The composition includes suberic acid or a pharmaceutically acceptable salt thereof as an active ingredient.

13 Claims, 8 Drawing Sheets
Specification includes a Sequence Listing.

A

× 100

| Dexamethasone (50 μM) | - | + | + |
| Suberic acid (100 μM) | - | - | + |

× 40

| Dexamethasone (50 μM) | - | + | + |
| Suberic acid (100 μM) | - | - | + |

A  Rectus femoris

Chow

HFD

Suberic acid

COMPOSITION FOR PREVENTING OR TREATING MUSCLE DISEASES, COMPRISING SUBERIC ACID OR PHARMACEUTICALLY ACCEPTABLE SALT THEREOF AS ACTIVE INGREDIENT

CROSS-REFERENCE TO RELATED APPLICATIONS

This application is a national phase application under 35 U.S.C. § 371 of International Application No. PCT/KR2018/000300, filed Jan. 5, 2018, which claims priority to and the benefit of Korean Patent Application No. 10-2017-0002501, filed on Jan. 6, 2017, the contents of which applications are incorporated herein by reference in their entirety.

FIELD OF THE DISCLOSURE

The present invention relates to a composition for preventing or treating a muscular disease, which includes suberic acid or a pharmaceutically acceptable salt thereof as an active ingredient.

DESCRIPTION OF RELATED ART

As Korea is becoming an aging society, it has an elderly population of 7.2% in 2000, and it is expected to become a super-aged society (with an elderly population of 20% or more) in 2050 (2013 Statistics of Aged People by the National Statistics Office). In humans, muscle mass decreases with age (approximately 10 to 15% by the age of 50 to 70, and approximately 30% or more by the age of 70 to 80), resulting in deteriorated muscular strength and muscle function, the process of which is referred to as senile sarcopenia. Senile sarcopenia causes disabilities and gait disturbances to limit the independent lives of the elderly. Also, sarcopenia reduces a basal metabolic rate to increase insulin resistance, promote the onset of type II diabetes mellitus, and increase the risk of hypertension and cardiovascular diseases 3 to 5 fold. In recent years, there are no drugs that are approved for treatment of sarcopenia, and a drug repositioning technique is currently under development, which involves applying myostatin inhibitors or the existing therapeutic agents for other diseases, which were approved by the FDA, to sarcopenia.

Muscles are mainly divided into skeletal muscle, cardiac muscle, and smooth muscle. Among these, the skeletal muscle is a tissue that is present in the highest amount in the human body, and accounts for 40 to 45% by weight. The skeletal muscle is attached to bone by tendons, and thus serves to create the movement or force of the bone. One muscle consists of a number of muscle fibers, and each of the muscle fibers consists of a number of myofibrils, each of which consists of actin and myosin filaments. As the actin and myosin filaments move while overlapping each other, the muscle may be shortened or lengthened, causing the contraction and relaxation of whole muscles. An increase in size of myofibrils refers to an increase in thickness of muscle fibers, which results in increased muscle mass.

The types of the muscle fibers constituting the muscle are mainly classified into type I, type IIA and type IIB muscle fibers, depending on a metabolic process in which ATP is generated, and a contraction velocity. The 'type I muscle fibers' have a slow contraction velocity and are rich in myoglobin and mitochondria, and are thus suitable for sustained, low intensity aerobic activity. The type II muscle fibers are referred to as red muscle fibers because they appear red, and typically belong to the soleus. On the other hand, the 'type IIB muscle fibers' are used for short bursts of high intensity anaerobic exercise because they have a rapid contraction velocity. The type IIB muscle fibers appear white due to a low content of myoglobin, and typically belong to the gastrocnemius. The 'type IIA muscle fibers' have intermediate characteristics of the two types of the aforementioned muscle fibers, and belong to the rectus femoris. With an increasing age, the compositions of the type I and II muscle fibers in different parts of muscles vary and all types of the muscle fibers decrease.

The skeletal muscle has a characteristic of being regenerated and maintained depending on the environment, but such a characteristic may be lost with age. As a result, muscle mass may be reduced and muscular strength may also be lost as aging progresses. Signaling systems involved in the growth and regeneration of muscles include signaling in which the synthesis of proteins is regulated through mediation of insulin like growth factor 1 (IGF-1)/AKT. When the IGF-1 receptor (IGF-1R) present in the muscle cell membranes is activated, a level of AKT phosphorylation is increased through IRS 1 and PI3K phosphorylation. Therefore, AKT phosphorylation activates mTORC phosphorylation. The activation of mTORC increases the phosphorylation of ribosomal protein S6 kinase beta-1 (p70S6K1) to increase mRNA translation, and simultaneously enhance the activity of eukaryotic translation initiation factor 4 G (eIF4G) and phosphorylate a eukaryotic translation initiation factor 4E binding protein 1 (4E-BP1) protein. The eIF4G and 4E-BP1 are involved in formation of an eIF4F complex. That is, eIF4G binds to eIF4A and eIF4E to form an eIF4F complex, whereas 4E-BP1 increases eIF4E in a free state because it inhibits an ability to bind to the eIF4E when it is phosphorylated. The eIF4E binds to other translation initiation factors (eIF4G and eIF4A) to form an eIF4F complex. The eIF4F complex thus formed stabilizes a ribosomal structure to promote translation initiation, resulting in increased synthesis of proteins (Bodine et al., Akt/mTOR pathway is a crucial regulator of skeletal muscle hypertrophy and can prevent muscle atrophy in vivo. Nature Cell Biology, 3, 1014-1019, 2001).

Also, AKT phosphorylation increases a level of eIF2B expression through glycogen synthase kinase 3 (GSK3) to not only promote the growth of muscle fibers, but also suppress muscle loss by inhibiting the expression of Forkhead Box O (FOXO) which is a transcription factor involved in protein degradation. Muscle loss is regulated by signal transduction mediated by a receptor of the TGF-β family, which includes myostatin, transforming growth factor beta (TGF-β), and activin. When a ligand binds to the TGF-β type II receptor, the type I receptor is phosphorylated. The phosphorylated type I receptor phosphorylates a Smad 2/3 complex, which ultimately activates the FOXO. The activated FOXO increases the expression of muscle RING-finger protein-1 (MURF1; a muscle-specific ubiquitin-ligase), Muscle Atrophy F-Box (MAFbx)/atrogin-1 genes, which serves to attach ubiquitin to a lysine position of a target protein to promote protein degradation, thereby inducing a decrease in muscle mass (Gumucio et al., Atrogin-1, MuRF-1, and sarcopenia. Endocrine, 43, 12-21, 2013).

There is an ongoing need to search for materials that have excellent muscle function-regulating activity and are safely applicable. However, single components derived from natural substances have not been developed as compositions for improving muscle function. Therefore, the present inventors have attempted to develop food materials that have effects of strengthening muscles and improving muscle loss by suppressing an action of degradation of muscle proteins and promoting the synthesis of the muscle proteins from natural substances having few side effects.

SUMMARY OF THE INVENTION

Therefore, it is one object of the present invention to provide a pharmaceutical composition for preventing or treating a muscular disease, promoting muscle differentiation, or regenerating or strengthening muscles, which includes suberic acid or a pharmaceutically acceptable salt thereof as an active ingredient.

It is another object of the present invention to provide a health functional food composition or a livestock feed composition for preventing a muscular disease or improving muscle function, promoting muscle differentiation, or regenerating or strengthening muscles, which includes suberic acid or a pharmaceutically acceptable salt thereof as an active ingredient.

It is still another object of the present invention to provide a cosmetic composition for improving muscle function, which includes suberic acid or a pharmaceutically acceptable salt thereof as an active ingredient.

It is yet another object of the present invention to provide a method of preventing or treating a muscular disease or a method of promoting muscle differentiation or regenerating or strengthening muscles, which includes administering or supplying a pharmaceutical composition, which includes administering or supplying a pharmaceutical composition, which includes suberic acid or a salt thereof as an active ingredient, to a subject.

It is yet another object of the present invention to provide a use of the composition, which includes suberic acid or a salt thereof as an active ingredient, for preventing or treating a muscular disease, promoting muscle differentiation, or regenerating or strengthening muscles.

The technical problems to be solved in the present invention are not limited to the above-described technical problems, and thus it should be understood that technical problems which are not described in this specification will be made apparent from the detailed description of the invention by those skilled in the art.

According to one aspect of the present invention, there is provided a pharmaceutical composition for preventing or treating a muscular disease, which includes suberic acid or a pharmaceutically acceptable salt thereof as an active ingredient.

According to one exemplary embodiment of the present invention, the composition may increase the expression of a p-4E-BP1 or p-p70S6K1 protein.

According to one exemplary embodiment of the present invention, the composition may decrease expression of MuRF1 (Muscle Ring-Finger Protein) or MaFbx (Muscle atrophy F-box).

According to one exemplary embodiment of the present invention, the muscular disease may be a muscular disease caused by muscle dysfunction, a decrease in muscle mass, muscle wasting, or muscle degeneration.

According to one exemplary embodiment of the present invention, the muscular disease may include one or more selected from the group consisting of atony, muscular atrophy, muscular dystrophy, myasthenia, cachexia, rigid spine syndrome, amyotrophic lateral sclerosis (Lou Gehrig's disease), Charcot-Marie-Tooth disease, and sarcopenia.

According to another aspect of the present invention, there is provided a pharmaceutical composition for promoting muscle differentiation or regenerating or strengthening muscles, which includes suberic acid or a pharmaceutically acceptable salt thereof as an active ingredient.

According to still another aspect of the present invention, there is provided a health functional food composition for preventing a muscular disease or improving muscle function, which includes suberic acid or a pharmaceutically acceptable salt thereof as an active ingredient.

According to yet another aspect of the present invention, there is provided a health functional food composition for promoting muscle differentiation or regenerating or strengthening muscles, which includes suberic acid or a pharmaceutically acceptable salt thereof as an active ingredient.

According to yet another aspect of the present invention, there is provided a livestock feed composition for preventing or ameliorating a muscular disease, which includes suberic acid or a pharmaceutically acceptable salt thereof as an active ingredient.

According to yet another aspect of the present invention, there is provided a livestock feed composition for promoting muscle differentiation or regenerating or strengthening muscles, which includes suberic acid or a pharmaceutically acceptable salt thereof as an active ingredient.

According to yet another aspect of the present invention, there is provided a cosmetic composition for improving muscle function, which includes suberic acid or a pharmaceutically acceptable salt thereof as an active ingredient.

According to yet another aspect of the present invention, there is provided a method of preventing or treating a muscular disease, which includes administering or supplying a pharmaceutical composition, which includes suberic acid or a salt thereof as an active ingredient, to a subject.

According to yet another aspect of the present invention, there is provided a method of promoting muscle differentiation or regenerating or strengthening muscles, which includes administering or supplying a composition, which includes suberic acid or a salt thereof as an active ingredient, to a subject.

According to yet another aspect of the present invention, there is provided a use of the composition, which includes suberic acid or a salt thereof as an active ingredient, for preventing or treating a muscular disease.

According to yet another aspect of the present invention, there is provided a use of the composition, which includes suberic acid or a salt thereof as an active ingredient, for promoting muscle differentiation or regenerating or strengthening muscles.

The present invention relates to a composition for preventing or treating a muscular disease or improving muscle function, which includes suberic acid or a pharmaceutically acceptable salt thereof as an active ingredient. In this case, the suberic acid can increase the expression of proteins associated with the synthesis of muscle proteins and an increase in muscle mass in muscle cells, and inhibit the expression of enzymes associated with the degradation of muscle proteins at mRNA levels. Therefore, the suberic acid can have an effect of increasing muscular strength through muscle differentiation, muscle regeneration, and an increase in muscle mass against muscular diseases caused by muscle dysfunction, muscle wasting, or muscle degeneration, and can control a decrease in muscle mass. As a result, the suberic acid can be used to prevent or treat a muscular disease, increase muscle differentiation, muscle regeneration and muscle mass, or improve muscle function.

BRIEF DESCRIPTION OF THE DRAWINGS

FIG. 1A shows the myotubes stained with a Giemsa-Wright stain, as photographed and visualized by a microscope (Bar=100 μm), FIGS. 1B to 1D shows the results of measuring a diameter (B), a fusion index (C) and a length (D) of the myotubes. In this case, the respective values are expressed as the mean±standard errors of three measurements performed in each of the wells in triplicate. P<0.05 indicates statistical significance.

FIG. 2A shows levels of p-4E-BP1, total 4E-BP1, p-p70S6K1, and total p70S6K1 proteins, and FIG. 2B shows expression levels of MaFbx and MuRF1 genes. In this case, the respective values are expressed as the mean±standard errors of three measurements performed in each of the wells in triplicate. P<0.05 indicates statistical significance.

DETAILED DESCRIPTION OF THE INVENTION

Figure 1A:
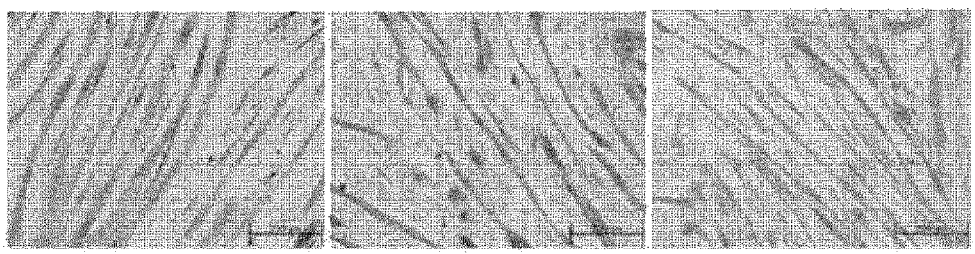
FIGS. 1A to 1D are graphs illustrating changes in thickness, length and fusion index of myotubes in a mouse myoblast cell line.
Figure 1A:
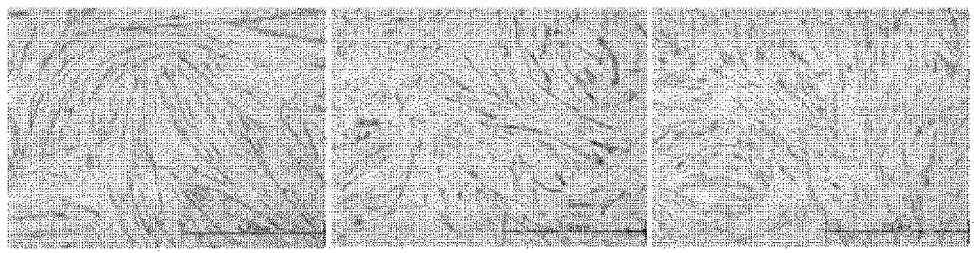

The present inventors have found that suberic acid, which is a type of dibasic acid, has effects of strengthening muscles and improving muscle loss by suppressing an action of degradation of muscle proteins and promoting the synthesis of the muscle proteins. Therefore, the present invention has been completed based on these facts.

In the present invention, the term "sinew" generally refers to a muscle, a tendon, and a ligament, and the term "muscle function" means an ability to exert a force by contraction of the muscle, and includes: muscular strength in which the muscle can exert the maximum contraction force so as to overcome resistance; muscular endurance strength which is an ability to exhibit how long or how many times the muscle can repeat a contraction/relaxation process at a given weight; and explosiveness which is an ability to exert a strong force within a short period of time. Such muscle function is managed by the liver and proportional to muscle mass, and the term "improvement of muscle function" refers to the improvement of the muscle function in a more positive direction.

Hereinafter, the present invention will be described in detail.

The present invention provides a pharmaceutical composition for preventing or treating a muscular disease, which includes suberic acid or a pharmaceutically acceptable salt thereof as an active ingredient.

Specifically, suberic acid is a component that is mainly included in plants such as *Ricinus communis* L. (a castor oil plant), *Quercus suber* (a cork tree), *Vernonia galamensis* (an ironweed), and the like, is a type of dibasic acid, and has a structural formula of $C_8H_{14}O_4$ and a molecular weight of 174.2 g/mol. Suberic acid may be represented by the following Formula 1, and has other names such as octanedioic acid, cork acid, 1,6-hexanedicarboxylic acid, and the like.

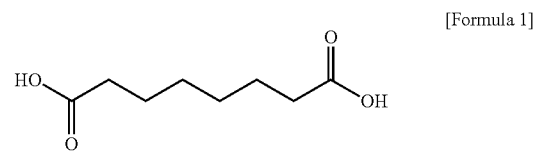 [SMILES: O=C(O)CCCCCCC(=O)O]

[Formula 1]

Also, the suberic acid may include suberic acid hydrates, suberic acid derivatives, and the like within a range having the same efficacy as the suberic acid, and may also include solvates or stereoisomers thereof.

A method of obtaining the suberic acid is not particularly limited, and types of suberic acid which are isolated from plants including the suberic acid, chemically synthesized using known manufacturing processes or commercially available may be used.

The composition according to the present invention may increase the expression of a p-4E-BP1 or p-p70S6K1 protein.

Also, the composition according to the present invention may decrease the expression of a muscle ring-finger protein (MuRF1) or muscle atrophy F-box (MaFbx). Specifically, the representative molecules associated with protein synthesis includes p70S6K1, 4E-BP1, and eIF members. The activities of the three molecules are regulated by upstream mTORC. The activation of mTORc phosphorylates p70S6K1, and the activated p70S6K1 phosphorylates 40S ribosomal protein S6 to increase mRNA translation. Also, the activation of mTORC increases the activity of eIF4G and simultaneously phosphorylates 4E-BP1. In this case, the two molecules are involved in formation of an eIF4F complex. That is, the eIF4G binds to eIF4A and eIF4E to form an eIF4F complex, whereas 4E-BP1 increases eIF4E in a free state because it inhibits an ability to bind to the eIF4E when it is phosphorylated. The eIF4E binds to other translation initiation factors (eIF4G and eIF4A) to form an eIF4F complex. The eIF4F complex thus formed stabilizes a ribosomal structure to promote translation initiation, resulting in increased synthesis of proteins. As muscle-specific ubiquitin ligases, MAFbx/Atrogin-1 and MuRF1 proteins are representative proteins that attach ubiquitin to a lysine position of a target protein to promote protein degradation, thereby inducing a decrease in muscle mass. In this case, the composition of the present invention may suppress a decrease in muscle mass by reducing the expression of the muscle ring-finger protein (MuRF1) or muscle atrophy F-box (MaFbx).

In the present invention, the "muscular disease" preferably includes diseases reported in the related art as the muscular disease caused by muscle dysfunction, a decrease in muscle mass, muscle wasting, or muscle degeneration. Specifically, the muscular disease may include one or more selected from the group consisting of atony, muscular atrophy, muscular dystrophy, myasthenia, cachexia, rigid spine syndrome, amyotrophic lateral sclerosis (Lou Gehrig's disease), Charcot-Marie-Tooth disease, and sarcopenia, but the present invention is not limited thereto. Also, the muscle wasting or degeneration is caused by factors such as innate factors, acquired factors, aging, and the like, and the muscle wasting is characterized by the progressive loss of muscle mass, and the weakening and degeneration of muscles, particularly, skeletal or voluntary muscle and cardiac muscle.

As long as the pharmaceutical composition for preventing or treating a muscular disease according to the present invention includes suberic acid or a pharmaceutically acceptable salt thereof, the content of the suberic acid is not particularly limited. Preferably, the content of the suberic acid may be set so that the suberic acid can be included at a concentration of 0.1 µM to 1,000 µM, but the present invention is not limited thereto. In this case, when the content of the suberic acid is below this concentration range, the synthesis and degradation activities of proteins in muscle cells may be degraded, which makes it difficult to exhibit an effect of preventing or treating the muscular disease. On the other hand, when the content of the suberic acid is above this concentration range, the suberic acid has serious concerns such as toxicity, including cytotoxicity.

The pharmaceutical composition for preventing or treating a muscular disease according to the present invention may be formulated into the forms of, for example, oral formulations such as powders, granules, tablets, capsules, suspensions, emulsions, syrups, aerosols, and the like, preparations for external use, suppositories, and sterile injectable solution, depending on conventional methods, and may be used. In this case, the pharmaceutical composition may include a suitable carrier, excipient, or diluent typically used to prepare a pharmaceutical composition for the purpose of formulation.

The carrier, excipient, or diluent may include various compounds or mixtures including lactose, dextrose, sucrose, sorbitol, mannitol, xylitol, erythritol, maltitol, starch, acacia gum, alginate, gelatin, calcium phosphate, calcium silicate, cellulose, methyl cellulose, amorphous cellulose, polyvinyl pyrrolidone, water, methyl hydroxybenzoate, propyl hydroxybenzoate, talc, magnesium stearate, mineral oil, and the like.

When formulated, the pharmaceutical composition may be prepared using a diluent or an excipient generally used in the art, such as a filler, an extending agent, a binding agent, a wetting agent, a disintegrating agent, a surfactant, and the like.

A solid preparation for oral administration may be prepared by mixing the suberic acid with at least one excipient, for example, starch, calcium carbonate, sucrose or lactose, gelatin, and the like. In addition to the simple excipients, lubricants such as magnesium stearate, talc, and the like may be used herein.

A liquid phase preparation for oral administration includes a suspension, a solution for internal use, an emulsion, a syrup, and the like. Such a liquid phase preparation may encompass various excipients, for example, a wetting agent, a sweetening agent, a flavoring agent, a preservative, and the like in addition to the inert diluents (for example, water, liquid paraffin) commonly used in the art.

A preparation for parenteral administration includes a sterile aqueous solution, a non-aqueous solvent, a suspension, an emulsion, a lyophilized preparation, a suppository, and the like. A vegetable oil such as propylene glycol, polyethylene glycol, or olive oil, or an injectable ester such as ethyl oleate may be used as the non-aqueous solvent and the suspension. Witepsol, Macrogol, Tween 61, cocoa butter, laurin butter, glycerol gelatin, and the like may be used as a base of the suppository.

The preferred dose of the pharmaceutical composition for preventing or treating a muscular disease according to the present invention may vary depending on the condition and weight of a patient, the severity of a disease, the form of a drug, a route of administration, and an administration time, but may be properly chosen by those skilled in the art. To show a beneficial effect, however, the pharmaceutical composition may be administered daily at a dose of 0.0001 to 2,000 mg/kg, preferably 0.001 to 2,000 mg/kg. The composition may be administered once a day, or administered in several divided doses. However, the scope of the present invention is not limited by the dose of the pharmaceutical composition.

The pharmaceutical composition for preventing or treating a muscular disease according to the present invention may be administered to mammals (for example, mice, rats, livestock, humans, and the like) through various routes of administration. The pharmaceutical composition may, for example, be administered through all modes of administration such as oral, rectal or intravenous, intramuscular, subcutaneous, intrauterine dural, or intracerebroventricular injection Also, the present invention provides a pharmaceutical composition for promoting muscle differentiation or regenerating or strengthening muscles, which includes suberic acid or a pharmaceutically acceptable salt thereof as an active ingredient. The details of the suberic acid are as described above.

The growth of the muscle may be realized through an increase in fiber size and/or an increase in number of fibers. The growth of the muscle may be determined by means of A) an increase in wet weight, B) an increase in protein content, C) an increase in number of muscle fibers, and D) an increase in diameter of muscle fibers. The increase in growth of the muscle fibers may be defined as an increase in diameter when the diameter is defined as the minor axis of a cross-cut ellipsoid. A useful therapeutic agent increases the wet weight, the protein content and/or the diameter by 10% or more, more preferably 50% or more, and most preferably 100% or more, in animals whose muscle is degenerated by at least 10%, compared to the control animals (i.e., animals having a degenerated muscle tissue, which have not been treated with a muscle building compound), which have been previously treated in a similar way. A compound that increases the growth of muscle fibers by increasing the number of the muscle fibers is useful as the therapeutic agent when it increase the number of the muscle fibers in a diseased tissue by at least 1%, more preferably at least 20%, and most preferably at least 50%. Such percentage values are relatively determined with respect to the basic level in untreated control mammals having no disease or muscles having no contralateral disease when the compound is administered to act locally.

The muscle regeneration refers to a process in which new muscle fibers are formed from myoblasts. A useful therapeutic agent for regeneration increases the number of new fibers by at least approximately 1%, more preferably at least 20%, and most preferably at least 50%, as described above.

The differentiation of muscle cells means the induction of a muscle developmental program which specifies components of the muscle fibers such as contractile organs (myofibrils). A useful therapeutic agent for differentiation increases the amounts of all the components of the muscle fibers in a diseased tissue by approximately 10% or more, more preferably 50% or more, and most preferably 100% or more, compared to the corresponding tissue from the control animal treated in similar way.

Specifically, according to one exemplary embodiment of the present invention, it can be seen that the number of myotubes in mouse myoblast cells significantly increases when the mouse myoblast cells reduced by dexamethasone are treated with suberic acid. That is, the suberic acid of the present invention may increase the thickness of the myotubes in the mouse myoblast cells to suppress muscle loss and promote muscle growth.

Also, it can be seen that, when the mouse myoblast cells reduced by dexamethasone are treated with suberic acid, the suberic acid significantly increases the expression of p-4E-BP1 and p-p70S6K proteins associated with protein synthesis, and also significantly decreases the expression of MuRF1 and Mafbx/atrogin-1 proteins that induce a decrease in muscle mass. That is, the suberic acid of the present invention may increase phosphorylation of 4E-BP1 and p70S6K proteins in the mouse myoblast cells and suppress the expression of MuRF1 and Mafbx/atrogin-1 genes, resulting in increased muscle mass.

Further, the present invention provides a health functional food composition for preventing a muscular disease or improving muscle function, which includes suberic acid or a pharmaceutically acceptable salt thereof as an active ingredient. The details of the suberic acid and the muscular disease are as described above.

Also, the present invention provides a health functional food composition for promoting muscle differentiation or regenerating or strengthening muscles, which includes suberic acid or a pharmaceutically acceptable salt thereof as an active ingredient. The details of the suberic acid are as described above.

In the health functional food for improving muscle function according to the present invention, when the suberic acid is used as an additive of the health functional food, the suberic acid may be added as is, or may be used in combination with other foods or food ingredients. In this case, the suberic acid may be properly used according to conventional methods. An amount of the active ingredient mixed may be properly determined according to the purpose of use, such as prophylaxis, health or therapy.

A formulation for health functional foods may be prepared into forms such as powders, granules, pills, tablets, and capsules, as well as forms such as general foods or drinks.

Types of the food are not particularly limited, and examples of foods to which the components may be added includes meat, sausage, bread, chocolate, candies, snacks, confectioneries, pizza, ramen, other noodles, gums, dairy products (including ice cream), various soups, beverages, tea, drinks, alcoholic beverages, and vitamin complexes. In this case, the food may include all types of food in a conventional sense.

In general, for preparation of foods or drinks, the suberic acid may be added at an amount of 15 parts by weight or less, preferably 10 parts by weight or less, based on 100 parts by weight of the raw materials. However, when the suberic acid may be taken for a long period of time for the purpose of health and hygiene or for the purpose of health regulation, the amount of the suberic acid may be less than or equal to this content range. Also, the suberic acid of the present invention has no problems in terms of safety because a fraction from a natural substance is used, thus, the suberic acid may also be used at an amount greater than this content range.

In the health functional food according to the present invention, a drink may contain various additional components such as flavoring agents or natural carbohydrates like conventional drinks. The aforementioned natural carbohydrates may include monosaccharides such as glucose, fructose, disaccharides such as maltose, sucrose, and polysaccharides such as dextrin, cyclodextrin, and sugar alcohols such as xylitol, sorbitol, erythritol, and the like. Natural sweetening agents (thaumatin, stevia extracts, etc.), and synthetic sweetening agents (saccharin, aspartame, etc.) may be favorably used as the sweetening agent. A proportion of the natural carbohydrate may be in a range of approximately 0.01 to 0.04 g, preferably approximately 0.02 to 0.03 g per 100 mL of the drink according to the present invention.

In addition to the components as described above, the health functional food for improving muscle function according to the present invention may contain various nutrients, vitamins, electrolytes, flavoring agents, coloring agents, pectic acid and salts thereof, alginic acid and salts thereof, organic acid, protective colloid thickening agents, pH control agents, stabilizing agents, preservatives, glycerin, alcohols, carbonating agents used for carbonated drinks, and the like. In addition, the health functional food for improving muscle function according to the present invention may contain flesh for preparing natural fruit juices, fruit juice beverages, and vegetable drinks. These components may be used alone or in combination. The ratios of such additives are generally selected within a range of 0.01 to 0.1 part by weight, based on 100 parts by weight of the health functional food of the present invention, but the present invention is not limited thereto.

Also, the present invention provides a livestock feed composition for preventing or ameliorating a muscular disease, which includes suberic acid or a pharmaceutically acceptable salt thereof as an active ingredient. The details of the suberic acid are as described above.

In addition, the present invention provides a livestock feed composition for promoting muscle differentiation or regenerating or strengthening muscles, which includes suberic acid or a pharmaceutically acceptable salt thereof as an active ingredient. The details of the suberic acid are as described above.

The livestock is preferably one livestock selected from the group consisting of a cow, a pig, a chicken, a duck, a goat, a sheep, and a horse, but the present invention is not limited thereto.

The feed composition may include feed additives. The feed additives of the present invention correspond to feed supplements in the Control of Livestock and Fish Feed Act.

In the present invention, the term "feed" may mean any natural or artificial diet, meal, and the like, or components of the meal, which an animal eats, ingests, and digests, or is suitable for eating, taking, and digesting.

Types of the feed are not particularly limited, and feed generally used in the related art may be used as the feed. Non-limiting examples of the feed include vegetable feed such as cereals, roots, food processing by-products, algae, fiber, pharmaceutical by-products, fats and oils, starch, gourds, or crop by-products; animal feed such as proteins, minerals, fats, minerals, oils, single cell proteins, zooplankton, or foods; and the like. These components may be used alone or in combination of two or more.

Also, the feed additives may further include a carrier available for monogastric animals. In the present invention, the feed additives may be added as is, or added in combination with known carriers, stabilizing agents, and the like. When necessary, various nutrients such as vitamins, amino acids, minerals, and the like, antioxidants, and other additives may also be added. The feed additives may be in a suitable shape of a powder, a granule, a pellet, a suspension, or the like. When the feed additives of the present invention are supplied, the feed additives may be supplied alone to monogastric animals, or may be mixed with the feed and supplied to the monogastric animals.

Further, the present invention provides a cosmetic composition for improving muscle function, which includes suberic acid or a pharmaceutically acceptable salt thereof as an active ingredient. The details of the suberic acid are as described above.

The cosmetic composition of the present invention contains suberic acid as the active ingredient, and may be prepared into forms such as basic cosmetic compositions (cleansing products such as lotions, creams, essences, cleansing foams, and cleansing water, packs, body oils), color cosmetic compositions (foundations, lipsticks, mascara, make-up bases), compositions for hair products (shampoos, rinses, hair conditioners, hair gels), and soap when used in combination with a dermatologically acceptable excipient.

For example, the excipient may include a skin emollient, a skin penetration enhancer, a coloring agent, a flavoring agent, an emulsifying agent, a thickening agent, and a solvent, but the present invention is not limited thereto. Also, the excipient may further include a fragrance, a pigment, a disinfectant, an antioxidant, a preservative, and a humectant, and may also include viscosity-increasing agents, mineral salts, synthetic polymer materials, and the like for the purpose of improving physical properties. For example, when the cosmetic composition of the present invention is prepared into face cleansing products and soap, the cosmetic composition may be easily prepared by adding the suberic acid to a conventional base for face cleansing products and soap. When a cream is prepared, the cream may be prepared by adding suberic acid or a salt thereof to a conventional oil-in-water-type cream base. Fragrances, chelating agents, pigments, antioxidants, preservatives, and the like; and synthetic or natural materials such as proteins, minerals, vitamins, and the like for the purpose of improving physical properties, may be additionally added to the cream. The content of the suberic acid contained in the cosmetic composition of the present invention is preferably in a range of 0.001 to 10% by weight, and more preferably 0.01 to 5% by weight, based on the total weight of the entire composition, but the present invention is not limited thereto. When the content is less than 0.001% by weight, it may be difficult to expect a desired anti-aging and anti-wrinkle effect. On the other hand, when the content is greater than 10% by weight, it may be difficult to prepare formulations in terms of safety.

Additionally, the present invention provides a method for preventing or treating a muscular disease, promoting muscle differentiation, or regenerating or strengthening muscles, which includes administering or supplying a pharmaceutical composition, which includes suberic acid or a salt thereof as an active ingredient, to a subject.

Further, the present invention provides a use of the composition, which includes suberic acid or a salt thereof as an active ingredient, for treating or preventing a muscular disease, promoting muscle differentiation, or regenerating or strengthening muscles.

As described above, the composition of the present invention, which includes suberic acid or a pharmaceutically acceptable salt thereof as the active ingredient, may suppress a decrease in muscle mass, and may have an effect of increasing the phosphorylation of 4E-BP1 and p70S6K proteins in mouse myoblast cells and suppressing the expression of MuRF1 and Mafbx/atrogin-1 genes, thereby increasing muscular strength through muscle differentiation, muscle regeneration, and an increase in muscle mass against muscular diseases caused by muscle dysfunction, muscle wasting, or muscle degeneration. Therefore, the composition of the present invention may be useful in preventing or treating a muscular disease, promoting muscle differentiation, increasing muscle regeneration and muscle mass, or improving muscle function.

EXAMPLES

Hereinafter, preferred embodiments are provided to aid in understanding the present invention. However, it should be understood that the following examples are merely intended to provide a better understanding of the present invention, and are not intended to limit the scope of the present invention.

Preparative Example: Cell Culture

A mouse myoblast cell line (C2C12 cells) was purchased from the American Type Culture Collection (ATCC, Manassas, Va., USA), and the purchased cells were cultured at 37° C. in a 5% $CO_2$ incubator using a 10% fetal bovine serum medium (Gibco-BRL). When the cultured cells reached 80% confluence, the cells were differentiated into myotubes using a 2% horse serum medium (Gibco-BRL).

Example 1

From the fourth day of differentiation, the cells were treated with 50 μM dexamethasone (dexa; Sigma) and 100 μM suberic acid (CAS Number 505-48-6, Sigma) for 2 days.

Comparative Example 1

The cells were treated with 50 μM dexamethasone (dexa; Sigma) in the same manner as in Example 1.

Experimental Example 1: Effects of Suberic Acid on Suppression of Muscle Loss Using Mouse Myoblast Cell Line (1) Giemsa-Wright Staining The myotubes prepared in Example 1 were washed twice with phosphate-buffered saline (PBS), and then immobilized with 100% methanol for 10 minutes. When the immobilization was completed, the myotubes were air-dried at room temperature for 10 minutes, and then stained for 30 minutes by dropwise addition of a Giemsa-Wright staining solution (ASAN Pharmaceutical Co., Ltd., Seoul) which is used to specifically stain myotubes.

(2) Measurement of Thickness, Length and Fusion Index of Myotubes

The myotubes thus stained were photographed at 100× and 40× magnifications using a fluorescence microscope (IX 71, Olympus), and then analyzed using Image J software (USA). Six regions in each well were randomly selected and photographed using a microscope. The thicknesses, lengths and fusion indexes of at least 100 myoblast cells in each well were analyzed (in triplicate/group).

Figure 1B:
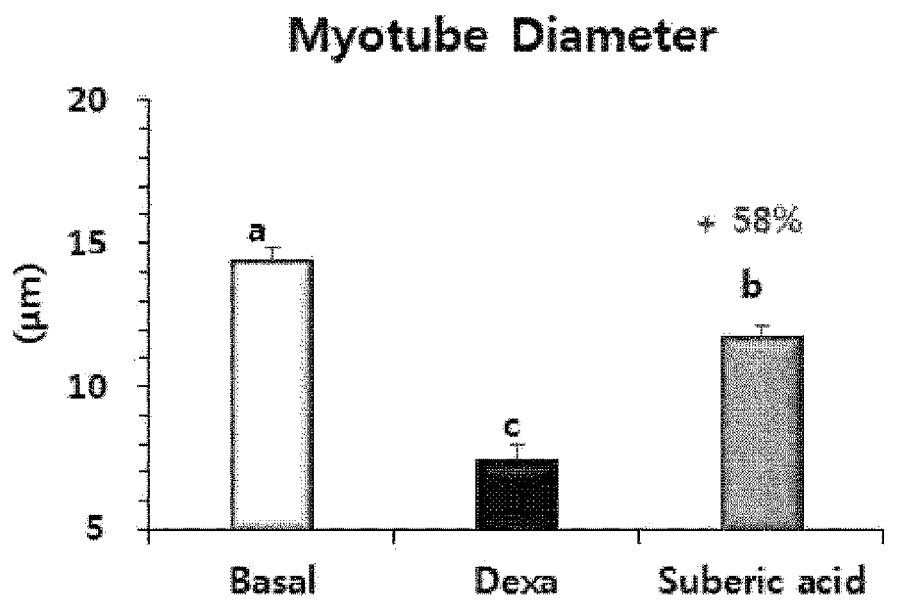
Figure 1C:
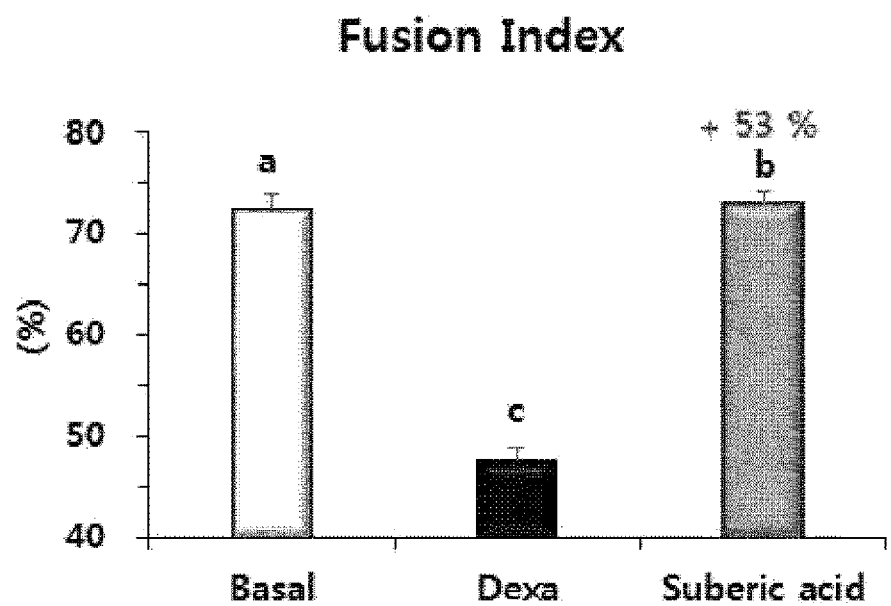
Figure 1D:
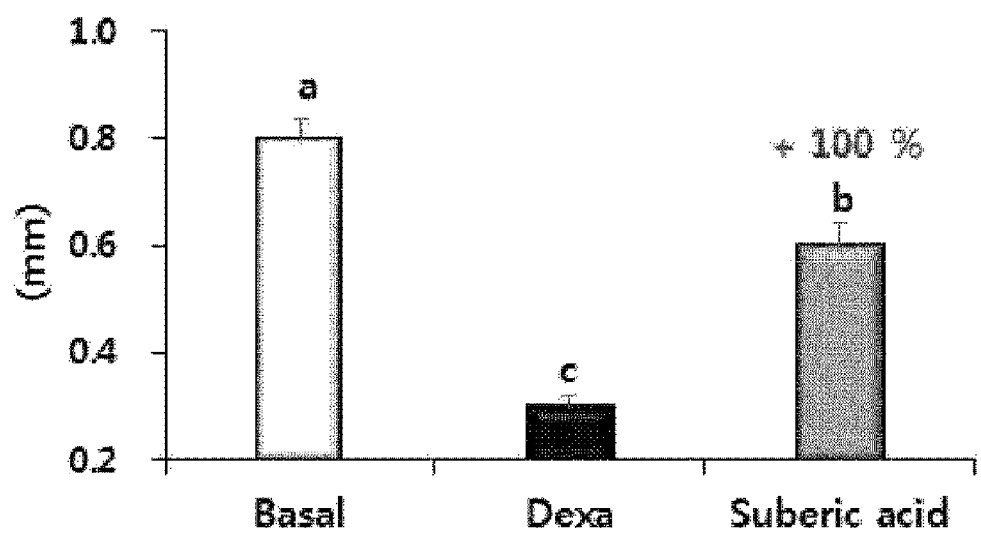

As a result, it can be visually observed that the thickness and length of the myotubes in the mouse myoblast cells remarkably decreased in the case of Comparative Example 1 compared to the normal cells (Basal), and the thickness and length of the myotubes reduced by dexamethasone increased again in the case of Example 1 in which the myotubes were treated with suberic acid, as shown in FIG. 1A. The results of quantitative determination of the thickness and length also showed that the suberic acid significantly increased the thickness (58%, FIG. 1B), the fusion index (53%, FIG. 1C), and length (100%, FIG. 1D) of the myotubes, which were significantly reduced by dexamethasone. From these results, it can be seen that the suberic acid increases the thickness of the myotubes in the mouse myoblast cells to suppress muscle loss and promote muscle growth.

Experimental Example 2: Identification of Mechanism of Action (1) RNA isolation and reverse transcription-polymerase chain reaction (RT-PCR) using TRIzol method $1 \times 10^7$ mouse myoblast cells were added to 334 μL of a TRIzol solution, and pulverized. Thereafter, the resulting cell solution was centrifuged at 4° C. and 12,000× g for 10 minutes. The supernatant was transferred to a new tube, and 67 μL of chloroform was added thereto, and vortexed. The supernatant was again transferred to a new tube, and isopropanol was added so that a ratio of the supernatant and isopropanol was 1:1. The tube was violently shaken ten times, and the supernatant was then left at room temperature for 15 minutes, and centrifuged at 4° C. and 12,000×g for 10 minutes. Then, the supernatant was removed, and 1 mL of 70% ethanol was added to the residual precipitate. Then resulting solution was centrifuged at 4° C. and 7,500×g for 5 minutes. After the ethanol was removed, the tube containing the RNA precipitate was dried at room temperature for 15 minutes, and the RNA pellet was dissolved in nuclease-free water. A concentration of the extracted RNA sample was measured at wavelengths of 260 nm and 280 nm using a UV/VIS spectrophotometer (Beckman coulter, DU730), and the integrity of the RNA sample was determined by means of agarose gel electrophoresis.

The RNA sample extracted from the mouse myoblast cells was subjected to reverse transcription using an oligo-dT primer and a superscript reverse transcriptase (GIBCO BRL, Gaithersburg, Md., USA) to synthesize cDNAs. PCR was performed using the cDNAs obtained through the reverse transcription as the template and 5'- and 3'-flanking sequences of cDNA of a gene to be amplified as the primers. In this case, the primer sequences used herein are listed in Table 1 below. 1 μL of the amplified PCR products were electrophoresed on a 1% agarose gel to determine DNA bands.

anesulfonyl fluoride, 2 μg/mL aprotinin, 1 μg/mL pepstatin A, and 1 μg/mL leupeptin, was added to each well from which a medium was removed, and the cell suspension was harvested, and then centrifuged at 4° C. and 1,300×g for 20 minutes. Thereafter, the middle layer was taken, and proteins were quantified according to the Bradford method (Bio-Rad). 40 μg of the proteins were electrophoresed on a SDS polyacrylamide gel, and transferred to a nitrocellulose membrane (Amersham, Buckinghamshire, UK). The membrane was repeatedly washed three times with tris-buffered saline and Tween 20 solution (TBS-T) for 10 minutes, and then blocked with 10% skim milk for 60 minutes. The membrane was put with a primary antibody diluted at a ratio of 1:1,000, cultured for 12 hours while gently stirring at 4° C., and washed with TBS-T. Then, the membrane was again put with a secondary antibody diluted at a ratio of 1:2,000, cultured for 60 minutes, and then washed. In this case, p70S6K1, phospho-p70S6K1 (p-p70S6K1), 4E-BP1, phospho-4E-BP1 (p-4E-BP1), and GAPDH (Cell Signaling Technology, Beverly, Mass., USA) were used as the primary antibodies. Finally, the proteins were visualized on an X-ray film using an ECL Western blot detection kit (RPN2106, Amersham, Arlington Heights, Ill., USA). The bands visualized on the X-ray film were scanned, and then quantified using Quantity One analysis software (Bio-Rad).

Figure 2A:
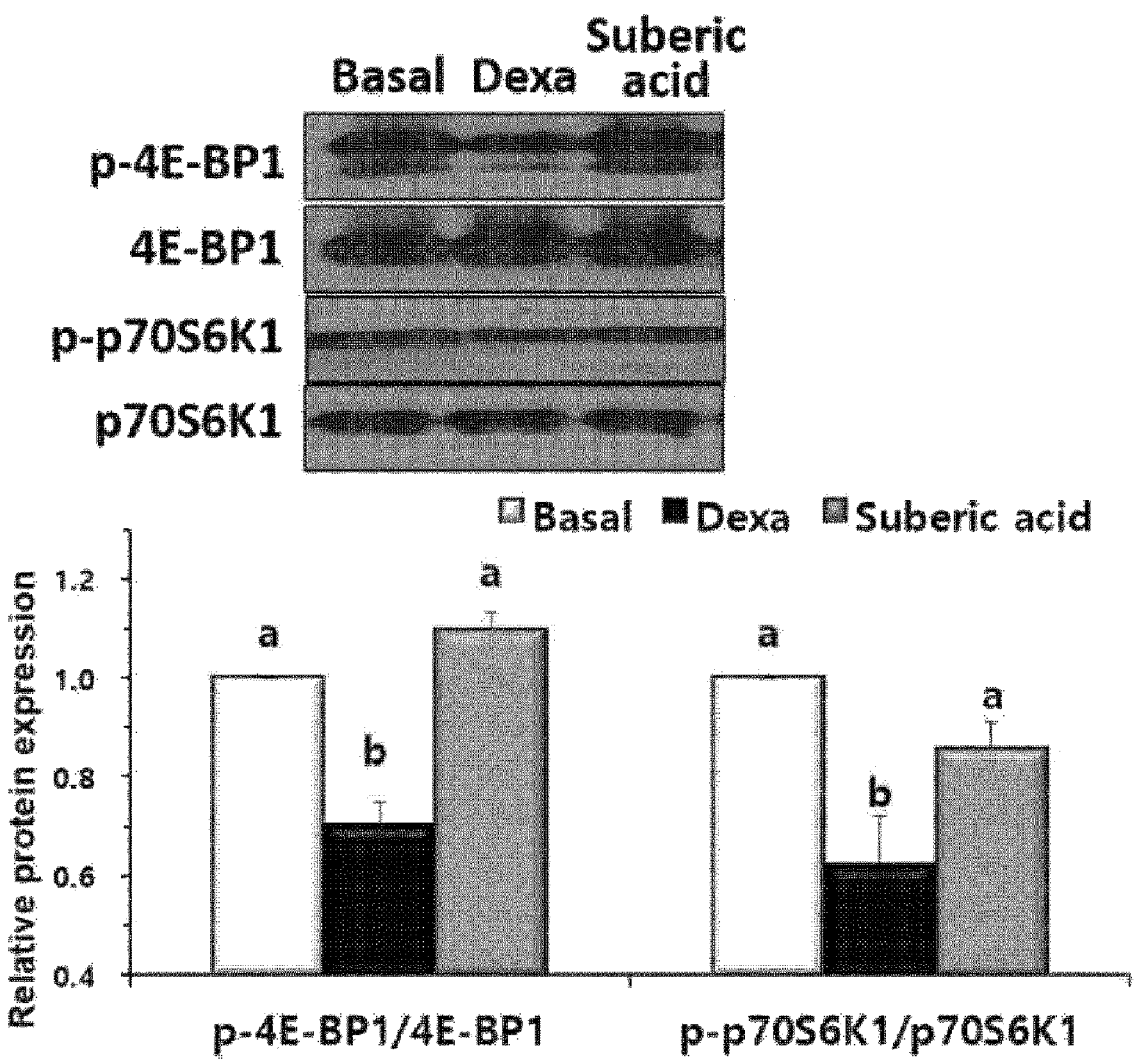
FIGS. 2A and 2B show changes in expression of molecules associated with the degradation and synthesis of proteins in a mouse myoblast cell line treated with suberic acid.
Figure 2B:
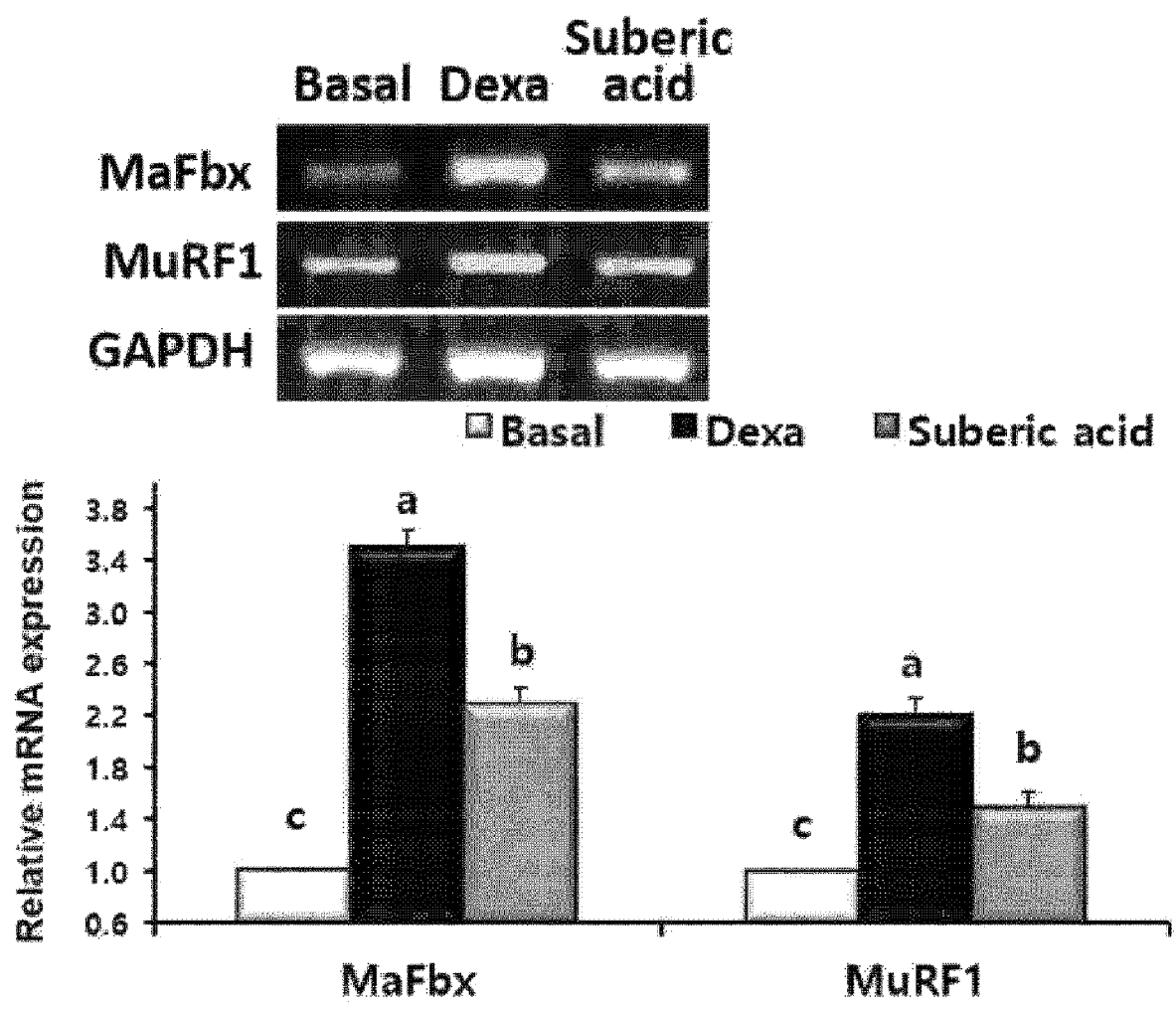

FIGS. 2A and 2B show changes in expression of molecules associated with the degradation and synthesis of proteins in a mouse myoblast cell line treated with suberic acid. As shown in FIG. 2, it can be seen that the amounts of the p-4E-BP1 and p-p70S6K1 proteins associated with protein synthesis significantly decreased in the case of Comparative Example 1, compared to the normal cells (Basal) (FIG. 2A), and the expression of the proteinase genes MaFbx/atrogin-1 and MuRF1 significantly increased (FIG. 2B). Also, it can be seen that the amounts of the p-4E-BP1 and p-p70S6K proteins reduced by dexamethasone significantly increased again (FIG. 2A), and the expression of the MuRF1 and MaFbx/atrogin-1 significantly decreased (FIG. 2B) in the case of Example 1 in which the cells were treated with suberic acid. That is, it was contemplated that the

TABLE 1

| Gene description | Primers | Sequences (5'→ 3') | Annealing temp. (° C.) | PCR product (bp) |
|---|---|---|---|---|
| MaFbx (synonym: atrogin-1) | F | GTCCAGAGAGTCGGCAAGTC (SEQ ID NO. 1) | 63 | 141 |
| | R | GTCGGTGATCGTGAGACCTT (SEQ ID NO. 2) | | |
| MuRF1 (synonym: TRAM63) | F | CTGAGCTGAGTAACTGCATC (SEQ ID NO. 3) | 60 | 147 |
| | R | AGAGGGTGTCAAACTTCTGA (SEQ ID NO. 4) | | |
| Glyceraldehyde 3-phosphate dehydrogenase (GAPDH) | F | GTGATGGCATGGACTGTGGT (SEQ ID NO. 5) | 55 | 163 |
| | R | GGAGCCAAAAGGGTCATCAT (SEQ ID NO. 6) | | |

(2) Western Blotting

To perform Western blotting in the cells, 500 μL of a lysis buffer, which included 100 mM Tris-HCl (pH 7.4), 5 mM EDTA, 50 mM sodium pyrophosphate, 50 mM NaF, 100 mM orthovanadate, 1% Triton X-100, 1 mM phenylmethsuberic acid was involved in increasing the phosphorylation of the 4E-BP1 and p70S6K1 proteins in the mouse myoblast cells and suppressing the expression of the MuRF1 and MaFbx/atrogin-1 genes, eventually resulting in increased muscle mass.

Experimental Example 3: Muscle-Strengthening Effect of Suberic Acid Using Mice

3-1. Experimental Methods

1) Preparation of Experimental Diets and Breeding of Laboratory Animals

Twenty-four 5-week-old male C57BL/6N mice (Mating, Korea) were adapted to laboratory circumstances for a week while feeding a commercially available normal diet (rodent chow), and then assigned into three groups (a Chow group, a HFD group, and a suberic acid-treated group; n=8 mice per group) according to a randomized block design, and bred for 10 weeks. An obesity-inducing diet used in this experiment was a high fat diet (HFD: 40% fat calories, 17 g of lard+3% corn oil/100 g of diet), and a suberic acid-supplemented high fat diet (Suberic Acid) had the same compositions as the HFD, provided that the suberic acid-supplemented high fat diet included 0.2% suberic acid (Table 2). A normal diet group (Chow) took a commercially available rodent chow. The suberic acid was purchased from Sigma-Aldrich Corp.

TABLE 2

| Ingredients | High fat diet (HFD) (g/kg diet) | Suberic acid-supplemented HFD (g/kg diet) |
| --- | --- | --- |
| Casein | 200 | 200 |
| DL-methionine | 3 | 3 |
| Corn starch | 111 | 109 |
| Sucrose | 370 | 370 |
| Cellulose | 50 | 50 |
| Corn oil | 30 | 30 |
| Lard | 170 | 170 |
| Vitamin complex | 12 | 12 |
| Mineral complex | 42 | 42 |
| Choline bitartrate | 2 | 2 |
| Cholesterol | 10 | 10 |
| tert-Butyl hydroquinone | 0.04 | 0.04 |
| Test material (suberic acid) | — | 2 |
| Total (g) | 1,000 | 1,000 |

2) Test for Measuring Grip Strength (Grip Test)

To measure grip strength of the mice, at 10 weeks of breeding, the grip strength of the mice was measured using four limbs. A force (N) generated by a mouse gripping a wire grid was measured a total of five times using a grip strength meter (Daejong Instrument Industry Co., Ltd., Korea) equipped with a wire grid (20×10 cm), and an at least one-minute break between every measurement was provided. The experimental results were calculated by dividing the measured force (N) by the weight (kg) of the mouse.

3) Immunohistochemical Staining of Muscle Tissue

A muscle tissue was extracted from a mouse, immobilized with 10% formalin, stained with a Hematoxylin and Eosin (H&E) stain, and then submitted to the Korea CFC (Gyeonggi-do, Korea). Thereafter, the stained muscle tissue was observed under an optical microscope (IX71, Olympus, JPN), and images were photographed using a digital camera (DP71, Olympus, JPN).

4) Statistical Analysis

The statistical analysis of all data was carried out using a statistical package for the social sciences (SPSS version 21.0, IBM, Armonk, N.Y., USA) PC package. In this case, the analyzed numerical values are expressed as the mean±SEM, and a significant difference between the groups was verified using ANOVA.

3-2. Experimental Results

Figure 3:
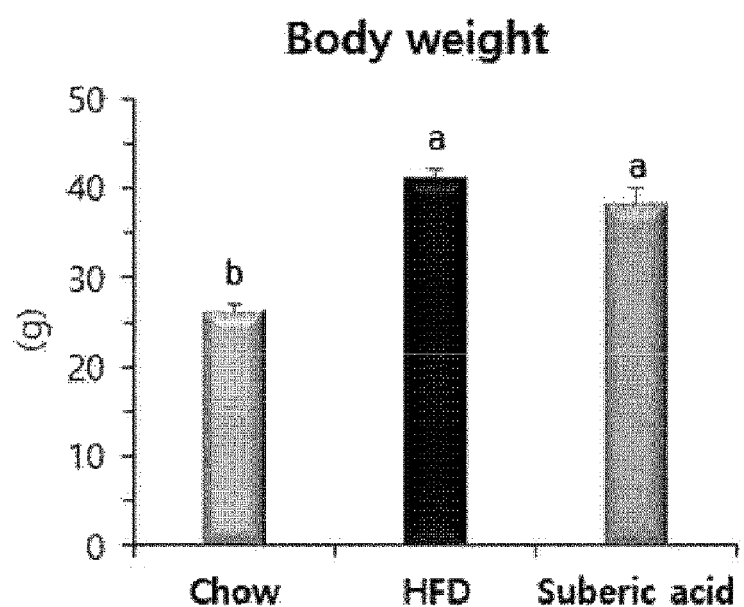
FIG. 3 shows the results of determining an increase in muscular strength caused by the intake of suberic acid from the changes in weights (A) and grip strengths (B) of mice in a normal diet group (Chow), a high-fat diet group (HFD), and a suberic acid intake group (Suberic acid).
Figure 3:
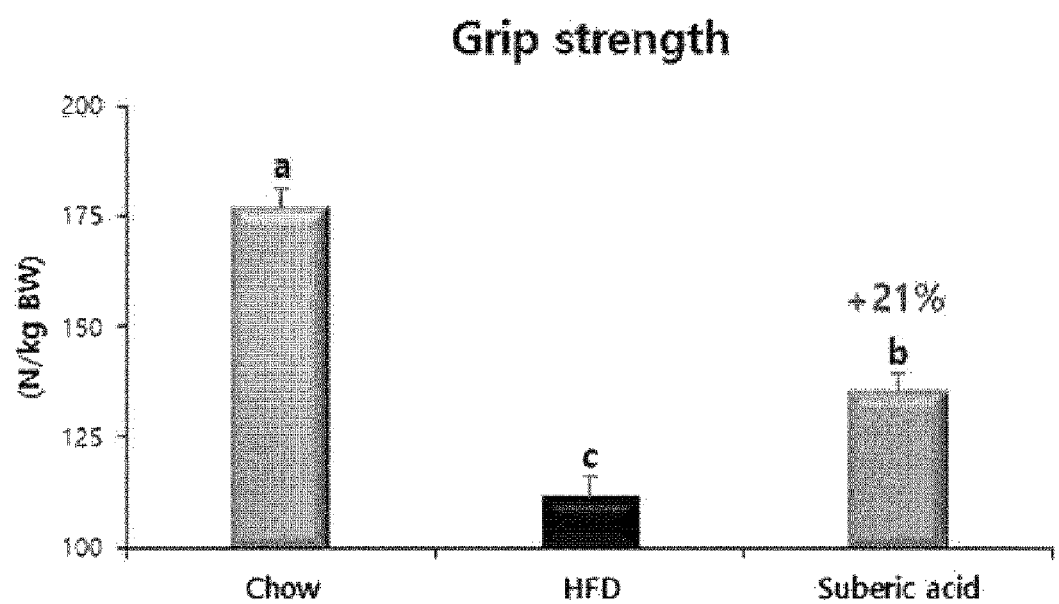

1) Confirmation of Increase in Muscular Strength of Mice by Intake of Suberic Acid The experimental results showed that the weights of the mice eating the suberic acid were not significantly different from those of the mice eating the high-fat diet (FIG. 3 (A)). Also, the suberic acid significantly increased the grip strength of the mice by approximately 21%, compared to the mice eating the high-fat diet (FIG. 3 (B)). From these results, it can be seen that the suberic acid had a very excellent muscle-strengthening effect in a high-fat diet-induced muscle loss animal model.

2) Changes in Fiber Diameter of Mouse Muscle Tissue by Intake of Suberic Acid

Figure 4:
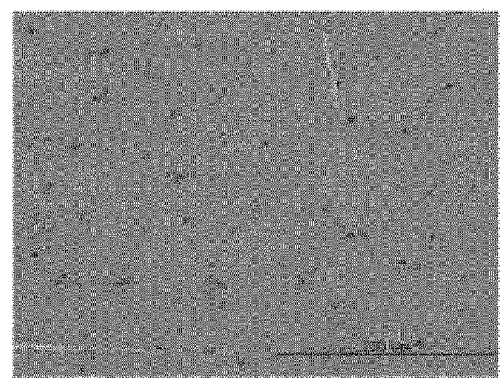
FIG. 4 shows the results of determining increases in fiber diameter of muscle tissues in the mouse rectus femoris (A) and soleus (B) caused by the intake of suberic acid. The quantitative values are expressed as the mean±standard errors of fiber diameters of muscles from eight mice. P<0.05 indicates statistical significance.
Figure 4:
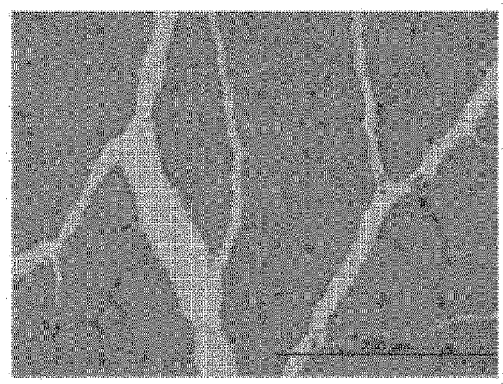
Figure 4:
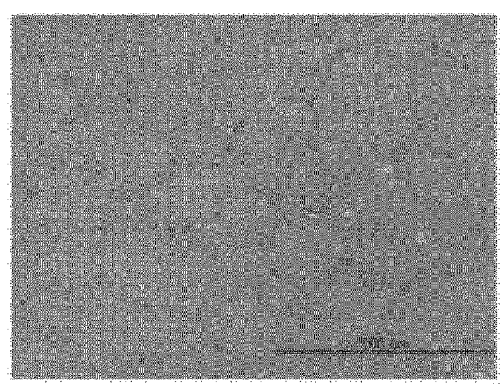
Figure 4:
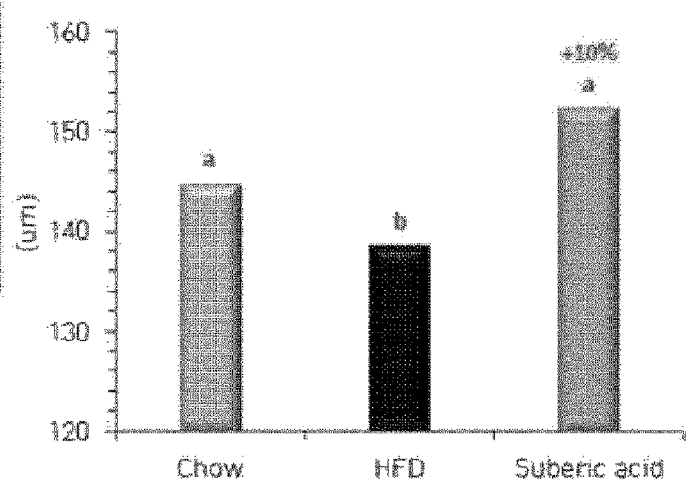
Figure 4:
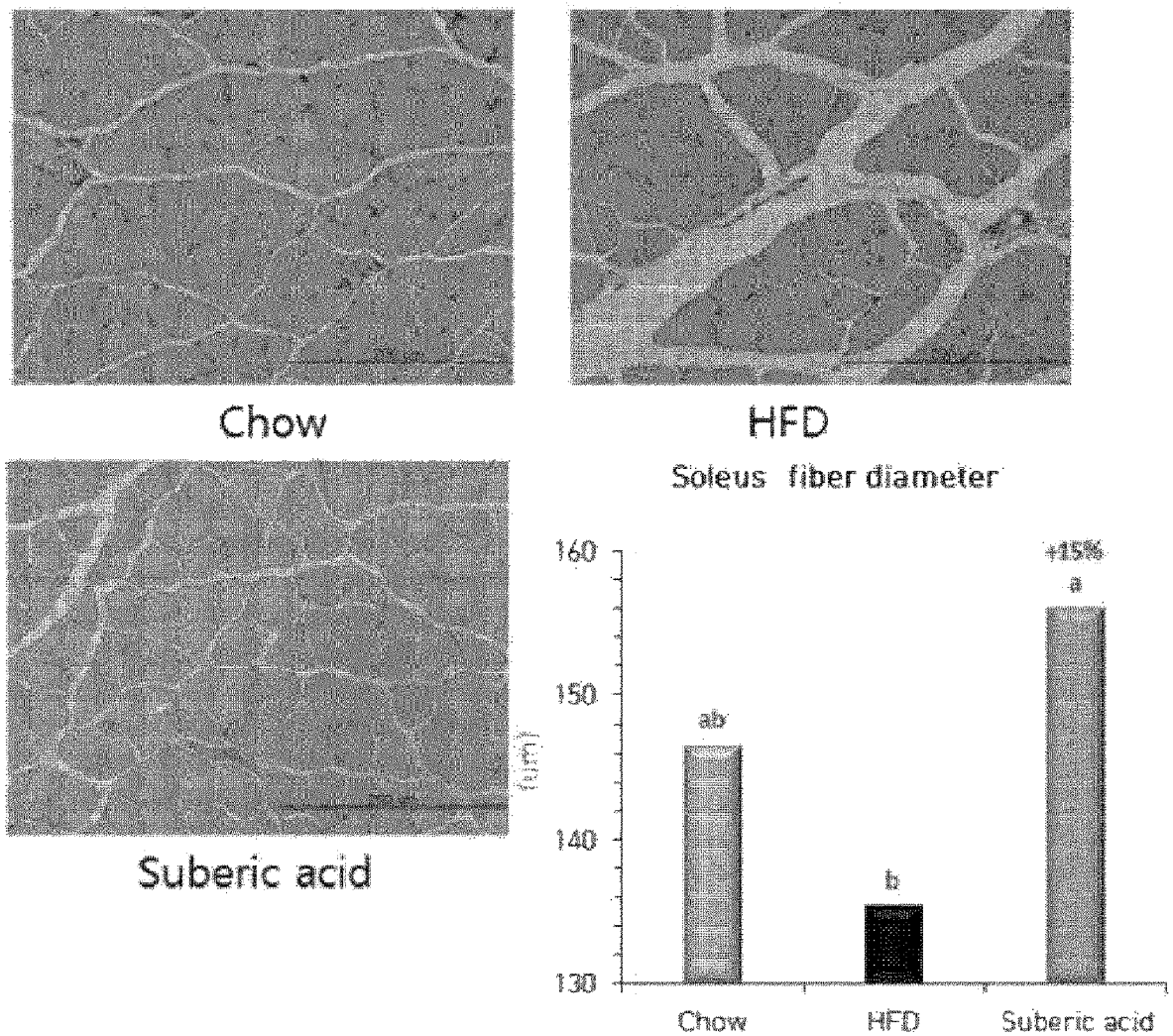

Also, the results of observation of mouse muscle tissues showed that the suberic acid significantly increased the fiber diameters of the rectus femoris (10%, FIG. 4 (A)) and the soleus (15%, FIG. 4 (B)) of the mice eating the high-fat diet. Therefore, it can be seen that the suberic acid had a very excellent effect of increasing skeletal muscle mass in a high-fat diet-induced muscle loss animal model.

Hereinafter, Formulation Examples of compositions including an extract of the present invention will be described. However, it should be understood that the Formulation Examples disclosed herein are intended to describe the present invention and not intended to limit the scope of the present invention.

Formulation Example 1: Preparation of Powder

| | |
| --- | --- |
| Suberic acid | 20 mg |
| Lactose hydrate | 100 mg |
| Talc | 10 mg |

The components were mixed, and filled in an airtight pack to prepare a powder.

Formulation Example 2: Preparation of Tablet

| | |
| --- | --- |
| Suberic acid | 10 mg |
| Corn starch | 100 mg |
| Lactose hydrate | 100 mg |
| Magnesium stearate | 2 mg |

The components were mixed, and then tablet-pressed to prepare a tablet according to a conventional method of preparing a tablet.

Formulation Example 3: Preparation of Capsule

| | |
| --- | --- |
| Suberic acid | 10 mg |
| Microcrystalline cellulose | 3 mg |
| Lactose hydrate | 14.8 mg |
| Magnesium stearate | 0.2 mg |

The components were mixed, and then filled in a gelatin capsule to prepare a capsule according to a conventional method of preparing a capsule.

Formulation Example 4: Preparation of Injection

| | |
|---|---|
| Suberic acid | 10 mg |
| Mannitol | 180 mg |
| Sterile distilled water for injection | 2974 mg |
| Monobasic sodium phosphate | 26 mg |

The components were mixed, and an injection was then prepared according to a conventional method of preparing an injection so that the aforementioned contents of the components were contained per ampoule (2 ml).

Formulation Example 5: Preparation of Solution

| | |
|---|---|
| Suberic acid | 10 mg |
| Isomerized sugar | 10 mg |
| Mannitol | 5 mg |
| Purified water | Suitable amount |
| Lemon flavor | Suitable amount |

A solution was prepared according to a conventional method of preparing a solution by dissolving the respective components in purified water, adding a suitable amount of lemon flavor, adding purified water to adjust a volume of the resulting mixture to 100 ml, sterilizing the mixture, and filling the mixture into a brown vial.

Formulation Example 6: Preparation of Health Functional Food

| | |
|---|---|
| Suberic acid | 10 mg |
| Vitamin blend | Suitable amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral blend | Suitable amount |
| Ferrous sulfate | 1.75 mg |
| Zinc oxide | 0.82 mg |
| Magnesium carbonate | 25.3 mg |
| Monobasic potassium phosphate | 15 mg |
| Dibasic calcium phosphate | 55 mg |
| Potassium citrate | 30 mg |
| Calcium carbonate | 100 mg |
| Magnesium chloride | 24.8 mg |

Although the compositional ratio of the vitamin and mineral blend was based on blending relatively suitable components for health food in a preferred embodiment, the blending ratio may be optionally varied. Then, the components were mixed according to a conventional method of preparing a health food to prepare granules, which may be used to prepare a health food composition according to a conventional method.

Formulation Example 7: Preparation of Health Drink

| | |
|---|---|
| Suberic acid | 10 mg |
| Vitamin C | 15 g |
| Vitamin E (powdery) | 100 g |
| Ferrous lactate | 19.75 g |
| Zinc oxide | 3.5 g |
| Nicotinamide | 3.5 g |
| Vitamin A | 0.2 g |
| Vitamin B1 | 0.25 g |
| Vitamin B2 | 0.3 g |
| Purified water | Balance |

The components were mixed, heated at 85° C. for approximately one hour while stirring according to a conventional method of preparing a health drink. Thereafter, the resulting solution was filtered and put into a 2 L sterile container. The solution was then sealed, sterilized and stored at a refrigeration temperature. The resulting solution was used to prepare a health drink composition according to the present invention.

Although the compositional ratio is based on blending relatively suitable components for desirable drinks in a preferred embodiment, the blending ratio may be optionally varied according to the regional or national preference of a consumer class or a consumer nation and to applications.

Hereinafter, Preparation Examples of cosmetic compositions including an extract of the present invention will be described. However, it should be understood that the Preparation Examples disclosed herein are intended to describe the present invention and not intended to limit the scope of the present invention.

Preparation Example 1: Nutritional Skin Lotion (Milk Lotion)

| | |
|---|---|
| Suberic acid | 2.0% by weight |
| Squalane | 5.0% by weight |
| Beeswax | 4.0% by weight |
| Polysorbate 60 | 1.5% by weight |
| Sorbitan sesquioleate | 1.5% by weight |
| Liquid paraffin | 0.5% by weight |
| Caprylic/capric triglyceride | 5.0% by weight |
| Glycerin | 3.0% by weight |
| Butylene glycol | 3.0% by weight |
| Propylene glycol | 3.0% by weight |
| Carboxyvinyl polymer | 0.1% by weight |
| Triethanolamine | 0.2% by weight |
| Preservative, pigment, fragrance | Suitable amounts |
| Purified water | to 100% by weight |

Although the blending ratio is based on blending relatively suitable components for a nutritional skin lotion in a preferred embodiment, the blending ratio may be optionally varied. Then, the nutritional skin lotion may be prepared according to the conventional preparation method in the field of cosmetics.

Preparation Example 2: Skin-Softening Lotion (Skin Lotion)

| | |
|---|---|
| Suberic acid | 2.0% by weight |
| Glycerin | 3.0% by weight |

-continued

| | |
|---|---|
| Butylene glycol | 2.0% by weight |
| Propylene glycol | 2.0% by weight |
| Carboxyvinyl polymer | 0.1% by weight |
| PEG 12 nonylphenyl ether | 0.2% by weight |
| Polysorbate 80 | 0.4% by weight |
| Ethanol | 10.0% by weight |
| Triethanolamine | 0.1% by weight |
| Preservative, pigment, fragrance | Suitable amounts |
| Purified water | to 100% by weight |

Although the blending ratio is based on blending relatively suitable components for a skin-softening lotion in a preferred embodiment, the blending ratio may be optionally varied. Then, the skin-softening lotion may be prepared according to a conventional preparation method in the field of cosmetics.

Preparation Example 3: Nourishing Cream

| | |
|---|---|
| Suberic acid | 2.0% by weight |
| Polysorbate 60 | 1.5% by weight |
| Sorbitan sesquioleate | 0.5% by weight |
| PEG 60 hydrogenated castor oil | 2.0% by weight |
| Liquid paraffin | 10% by weight |
| Squalane | 5.0% by weight |
| Caprylic/capric triglyceride | 5.0% by weight |
| Glycerin | 5.0% by weight |
| Butylene glycol | 3.0% by weight |
| Propylene glycol | 3.0% by weight |
| Triethanolamine | 0.2% by weight |
| Preservative | Suitable amount |
| Pigment | Suitable amount |
| Fragrance | Suitable amount |
| Purified water | to 100% by weight |

Although the blending ratio is based on blending relatively suitable components for a nourishing cream in a preferred embodiment, the blending ratio may be optionally varied. Then, the nourishing cream may be prepared according to a conventional preparation method in the field of cosmetics.

Preparation Example 4: Massage Cream

| | |
|---|---|
| Suberic acid | 1.0% by weight |
| Beeswax | 10.0% by weight |
| Polysorbate 60 | 1.5% by weight |
| PEG 60 hydrogenated castor oil | 2.0% by weight |
| Sorbitan sesquioleate | 0.8% by weight |
| Liquid paraffin | 40.0% by weight |
| Squalane | 5.0% by weight |
| Caprylic/capric triglyceride | 4.0% by weight |
| Glycerin | 5.0% by weight |
| Butylene glycol | 3.0% by weight |
| Propylene glycol | 3.0% by weight |
| Triethanolamine | 0.2% by weight |
| Preservative, pigment, fragrance | Suitable amount |
| Purified water | to 100% by weight |

Although the blending ratio is based on blending relatively suitable components for a massage cream in a preferred embodiment, the blending ratio may be optionally varied. Then, the massage cream may be prepared according to a conventional preparation method in the field of cosmetics.

Preparation Example 5: Pack

| | |
|---|---|
| Suberic acid | 1.0% by weight |
| Polyvinyl alcohol | 13.0% by weight |
| Sodium carboxymethyl cellulose | 0.2% by weight |
| Glycerin | 5.0% by weight |
| Allantoin | 0.1% by weight |
| Ethanol | 6.0% by weight |
| PEG 12 nonylphenyl ether | 0.3% by weight |
| Polysorbate 60 | 0.3% by weight |
| Preservative, pigment, fragrance | Suitable amount |
| Purified water | to 100% by weight |

Although the blending ratio is based on blending relatively suitable components for a pack in a preferred embodiment, the blending ratio may be optionally varied. Then, the pack may be prepared according to a conventional preparation method in the field of cosmetics.

Preparation Example 6: Gel

| | |
|---|---|
| Suberic acid | 0.5% by weight |
| Sodium ethylenediamine acetate | 0.05% by weight |
| Glycerin | 5.0% by weight |
| Carboxyvinyl polymer | 0.3% by weight |
| Ethanol | 5.0% by weight |
| PEG 60 hydrogenated castor oil | 0.5% by weight |
| Triethanolamine | 0.3% by weight |
| Preservative, pigment, fragrance | Suitable amount |
| Purified water | to 100% by weight |

Although the blending ratio is based on blending relatively suitable components for a gel in a preferred embodiment, the blending ratio may be optionally varied. Then, the gel may be prepared according to a conventional preparation method in the field of cosmetics.

Although the blending ratios are based on blending relatively suitable components for cosmetic compositions in preferred embodiments, they may be applied to various cosmetic applications including other color cosmetics. Also, the blending ratios may be used to prepare drugs, that is, ointments that may be applied on the human body according to the efficacy thereof, and may be optionally varied according to the regional or national preference of a consumer class or a consumer nation and to applications.

Hereinafter, Preparation Examples of livestock feed compositions including an extract of the present invention will be described. However, it should be understood that the Preparation Examples disclosed herein are intended to describe the present invention and not intended to limit the scope of the present invention.

Preparation Example 7: Preparation of Feed Additive

| | |
|---|---|
| Composition | 0.1 to 10% |
| Tricalcium phosphate | 1 to 20% |
| Vitamin E | 0.01 to 0.1% |
| Enzyme powder | 1 to 10% |
| *Lactobacillus* sp. | 0.1 to 10% |
| Glucose | 20 to 90% |

Preparation Example 8: Preparation of Feed

A feed was prepared with the following composition using the feed additive of Preparation Example 1 as an active ingredient.

| | |
|---|---|
| Feed additive of Preparation Example 1 | 0.1 to 10% |
| Wheat bran | 40 to 49.9% |
| Milo | 21.20% |
| Soybean meal | 20.00% |
| Fish meal | 3.00% |
| Molasses | 4.00% |
| Mineral | 1.53% |
| Vitamins | 0.27% |

The above description of the present invention are given by way of illustration only, and it should be understood by those skilled in the art to which the present invention belongs that various changes and modifications can be made without departing from the technical spirit and scope of the present invention. Therefore, it should be understood that the aforementioned embodiments are given by way of illustration only, and are not intended to be limiting in all aspects.

The invention claimed is:

1. A method for preventing or treating a muscular disease, the method comprising: administering a composition which comprises suberic acid or a pharmaceutically acceptable salt thereof as an active ingredient to a subject in need thereof.

2. The method of claim 1, wherein the composition increases the expression of a p-4E-BP1 or p-p70S6K1 protein in the subject in need thereof.

3. The method of claim 1, wherein the composition decreases the expression of MuRF1 (Muscle Ring-Finger Protein) or MaFbx (Muscle atrophy F-box) in the subject in need thereof.

4. The method of claim 1, wherein the muscular disease is a muscular disease caused by muscle dysfunction, a decrease in muscle mass, muscle wasting, or muscle degeneration.

5. The method of claim 1, wherein the muscular disease comprises one or more selected from the group consisting of atony, muscular atrophy, muscular dystrophy, myasthenia, cachexia, rigid spine syndrome, amyotrophic lateral sclerosis (Lou Gehrig's disease), Charcot-Marie-Tooth disease, and sarcopenia.

6. The method of claim 1, wherein the composition is a pharmaceutical composition, a health functional food composition, or a livestock feed composition.

7. A method for promoting muscle differentiation or regenerating or strengthening muscles, the method comprising: administering a composition, which comprises suberic acid or a pharmaceutically acceptable salt thereof as an active ingredient to a subject in need thereof.

8. The method of claim 7, wherein the composition is a pharmaceutical composition, a health functional food composition, or a livestock feed composition.

9. A method for improving muscle function, the method comprising administering a composition, which comprises suberic acid or a pharmaceutically acceptable salt thereof as an active ingredient to a subject in need thereof, wherein the composition is administered topically.

10. The method of claim 1, wherein the composition is administered orally.

11. The method of claim 1, wherein the composition is administered topically.

12. The method of claim 7, wherein the composition is administered orally.

13. The method of claim 7, wherein the composition is administered topically.

* * * * *

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic nucleic acid - MaFbx_F primer

<400> SEQUENCE: 1
gtccagagag tcggcaagtc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic nucleic acid - aFbx_R primer

<400> SEQUENCE: 2
gtcggtgatc gtgagacctt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic nucleic acid - MuRF1_F primer

<400> SEQUENCE: 3
ctgagctgag taactgcatc                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic nucleic acid - MuRF1_R primer

<400> SEQUENCE: 4
agagggtgtc aaacttctga                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic nucleic acid - GAPDH_F primer

<400> SEQUENCE: 5
gtgatggcat ggactgtggt                                              20
```

```
<210> SEQ ID NO 6
<211> LENGTH: 20
<212> TYPE: DNA
<213> ORGANISM: Artificial Sequence
<220> FEATURE:
<223> OTHER INFORMATION: Synthetic nucleic acid - GAPDH_R primer

<400> SEQUENCE: 6
ggagccaaaa gggtcatcat                                              20
```